United States Patent
Dussich et al.

(10) Patent No.: US 10,100,180 B2
(45) Date of Patent: Oct. 16, 2018

(54) SCENT EXTENDED ANIMAL-REPELLING SYNTHETIC RESIN COMPOSITION

(71) Applicant: MINT-X LLC, College Point, NY (US)

(72) Inventors: James A. Dussich, New York, NY (US); Joseph A. Dussich, Jr., New York, NY (US)

(73) Assignee: MINT-X LLC, College Point, NY (US)

( * ) Notice: Subject to any disclaimer, the term of this patent is extended or adjusted under 35 U.S.C. 154(b) by 58 days.

(21) Appl. No.: 15/241,822

(22) Filed: Aug. 19, 2016

(65) Prior Publication Data

US 2017/0051137 A1 Feb. 23, 2017

Related U.S. Application Data

(60) Provisional application No. 62/208,695, filed on Aug. 22, 2015.

(51) Int. Cl.

| | |
|---|---|
| *C08L 23/06* | (2006.01) |
| *A01N 25/10* | (2006.01) |
| *C08J 3/22* | (2006.01) |
| *C08L 21/00* | (2006.01) |
| *C08K 3/34* | (2006.01) |
| *C08L 23/08* | (2006.01) |

(52) U.S. Cl.
CPC .............. *C08L 23/06* (2013.01); *A01N 25/10* (2013.01); *C08J 3/226* (2013.01); *C08K 3/34* (2013.01); *C08L 21/00* (2013.01); *C08L 23/0853* (2013.01); *C08J 2300/26* (2013.01); *C08J 2323/06* (2013.01); *C08J 2405/16* (2013.01); *C08J 2423/08* (2013.01); *C08L 2205/02* (2013.01); *C08L 2205/03* (2013.01); *C08L 2207/04* (2013.01); *C08L 2310/00* (2013.01)

(58) Field of Classification Search
CPC ...................................................... A01N 25/10
See application file for complete search history.

(56) References Cited

U.S. PATENT DOCUMENTS

| | | |
|---|---|---|
| 3,553,296 A | 1/1971 | Gaeckel |
| 4,017,630 A | 4/1977 | Lemin et al. |
| 4,555,015 A | 11/1985 | Haase |
| 4,961,929 A | 10/1990 | Gurvich et al. |
| 5,013,551 A | 5/1991 | Atkinson |
| 5,041,421 A | 8/1991 | King |
| 5,571,582 A | 11/1996 | Katoh |
| 6,231,937 B1 | 5/2001 | Rader et al. |
| 6,337,081 B1 | 1/2002 | Warberg |
| 6,395,290 B2 | 5/2002 | Brown |
| 7,037,515 B2 | 5/2006 | Kalafsky et al. |
| 7,811,597 B2 | 10/2010 | Katoh et al. |
| 8,734,819 B2 | 5/2014 | Dussich, Jr. et al. |
| 2002/0094444 A1 | 7/2002 | Nakata et al. |
| 2003/0055179 A1 | 3/2003 | Ota et al. |
| 2006/0110421 A1 | 5/2006 | Katoh et al. |
| 2007/0065053 A1 | 3/2007 | Feinberg |
| 2007/0248688 A1 | 10/2007 | La Torre |
| 2010/0260872 A1 | 10/2010 | Dussich, Jr. et al. |

FOREIGN PATENT DOCUMENTS

| | | |
|---|---|---|
| CA | 2802515 A1 | 7/2014 |
| JP | H1112105 A | 1/1999 |
| WO | WO-200193814 A2 | 12/2001 |

OTHER PUBLICATIONS

ISA/US International Search Report and Written Opinion for Co-Pending International Application No. PCT/US16/50504, dated Feb. 3, 2017 (10 pgs).
ISA/US International Search Report and Written Opinion for Corresponding International Application No. PCT/US16/48012, dated Nov. 3, 2016 (8 pgs).
Regiert, Manies, "More than just smell—Slow-release system exploits functional properties of fragrances in coatings", 2007, European Coatings Journal, vol. No. 2 (9 pgs).
Wikipedia, "Cyclodextrin" (Jul. 21, 2015) [online] [retrieved on Oct. 14, 2016]. Retrieved from the internet <URL: https://en.wikipedia.org/w/index.php?title-Cyclodextrin&oldid=672437861> (7 pgs).
Co-pending U.S. Appl. No. 15/255,747, filed Sep. 2, 2016.

*Primary Examiner* — Edward J Cain
(74) *Attorney, Agent, or Firm* — Harris Beach PLLC

(57) ABSTRACT

An article that repels animals includes a synthetic resin composition. The synthetic resin composition includes a first thermoplastic polymer. A master blend is combined with the first thermoplastic polymer. The master blend includes a second thermoplastic polymer. At least one odorant compound is selected from the group consisting of a salicylic acid ester, menthol, corn mint oil, eucalyptus oil, camphor oil, and combinations thereof. At least one scent extender compound includes at least one cyclodextrin compound, wherein a ratio by weight of the second thermoplastic polymer to a combination of the odorant compound and the scent extender compound is about 2:1. A method for forming a master blend, a method for forming a synthetic resin composition, and an article that repels animals including a synthetic resin composition are also described.

20 Claims, No Drawings

SCENT EXTENDED ANIMAL-REPELLING SYNTHETIC RESIN COMPOSITION

CROSS-REFERENCE TO RELATED APPLICATIONS

This application claims priority to and the benefit of U.S. provisional patent application Ser. No. 62/208,695, IMPROVED ANIMAL-REPELLING SYNTHETIC RESIN COMPOSITION, filed Aug. 22, 2015, which application is incorporated herein by reference in its entirety.

FIELD OF THE APPLICATION

The application relates to an article that repels animals comprising a synthetic resin composition and particularly to a scent extended synthetic resin composition.

BACKGROUND

In many cities, the disposal of residential garbage is carried out as follows: each household puts its garbage into a polyethylene garbage bag designated by the city and places the filled bag in a designated spot outside the house on an appointed day for collection. The garbage bags are then collected by city garbage trucks.

A problem associated with this conventional disposal method is that garbage bags left outside are often ripped open by foraging animals like cats, dogs, rats, squirrels, and raccoons before garbage trucks can collect them, thereby scattering the garbage on the streets and sidewalks.

Industrial stretch wraps and films are highly elasticized plastic film that are wrapped around items for shipping and handling purposes. It is frequently used to unitize pallet loads but may also be used for bundling smaller items. Shrink wrap has similar uses, but is generally applied loosely around an item and shrinks tightly upon the application of heat.

There are similar known problems with wiring insulation. For example, in building construction, cable such as electrical cable comprising an insulator sheath made from synthetic resin typically is laid in ceilings or under floors where it is susceptible to being bitten by rats and squirrels infesting the building. As a result of the insulation being stripped off the wiring, electricity leakage, short-circuits, and fires may take place. For another example, backpackers leaving their vehicles unattended in parking lots for several days may return to find that the insulation has been chewed from the vehicle wiring harness by wild rodents.

A number of animal repellents are known, but none of them are satisfactory both in terms of effect and cost. In the prior art, repellents typically are impregnated into a powdery support, spread or sprayed directly on an article, or manufactured as a component of shaped articles having a repellent effect.

SUMMARY

According to one aspect, an article that repels animals includes a synthetic resin composition. The synthetic resin composition includes a first thermoplastic polymer. A master blend is combined with the first thermoplastic polymer. The master blend includes a second thermoplastic polymer. At least one odorant compound is selected from the group consisting of a salicylic acid ester, menthol, corn mint oil, eucalyptus oil, camphor oil, and combinations thereof. At least one scent extender compound includes at least one cyclodextrin compound, wherein a ratio by weight of the second thermoplastic polymer to a combination of the odorant compound and the scent extender compound is about 2:1.

In one embodiment, the scent extender compound includes at least one of: alpha-cyclodextrin, beta-cyclodextrin, hydroxypropyl-beta-cyclodextrin, and methyl-beta-cyclodextrin.

In another embodiment, the article includes a synthetic resin composition at between about 10 parts per million and about 15,000 parts per million by weight based on a total weight of the synthetic resin composition.

In yet another embodiment, the combination thereof includes, by weight, 32% to 40% methyl salicylate, 32% to 40% by weight of corn mint oil, 19% to 27% by weight of camphor oil, and 1% to 8% by weight of eucalyptus oil, all based on a total weight of the combination thereof.

In yet another embodiment, the combination thereof includes, by weight, about 36% methyl salicylate, about 36% corn mint oil, about 23% white camphor oil, and about 5% eucalyptus oil all based on a total weight of the combinations thereof.

In yet another embodiment, the article is selected from the group consisting of garbage bag, stretch wrap, shrink wrap, and electrical wiring insulation.

In yet another embodiment, the first thermoplastic polymer includes a polyolefin or a polyethylene.

In yet another embodiment, the first thermoplastic polymer includes an elastomer.

In yet another embodiment, the elastomer is selected from the group consisting of ethylene/propylene rubber (EPR), very low density polyethylene (VLDPE), hydrogenated styrene/butadiene block copolymer (SEES), polybutadiene, ethylene/ester of acrylic acid copolymer, ethylene/butene copolymer, ethylene/1-hexene copolymer, ethylene/1-octene copolymer, butadiene/styrene copolymer, isoprene/styrene copolymer, and hydrogenated isoprene/styrene copolymer.

In yet another embodiment, the second thermoplastic polymer includes a polyolefin or an ethyl/vinyl acetate copolymer.

In yet another embodiment, the synthetic resin composition further includes a filler.

In yet another embodiment, the filler is selected from the group consisting of diatomaceous earth, silica gel, synthetic zeolite, aluminum oxide, hydrotalcite, calcium carbonate, talc, natural zeolite, wollastonite, calcium sulfate, magnesium hydroxide, aluminum hydroxide, titanium dioxide, and carbon black.

According to another aspect, a method for forming a master blend, includes the steps of: selecting an amount of a pelleted ethylene/vinyl acetate copolymer; and adding a combination of an amount of a scent extender and an amount of at least one odorant compound selected from the group consisting of a salicylic acid ester, menthol, corn mint oil, eucalyptus oil, camphor oil, and combinations thereof to the pelleted ethylene/vinyl acetate copolymer in a weight ratio of 2 parts combination to 1 part ethylene/vinyl acetate copolymer, and blending the pelleted ethylene/vinyl acetate copolymer and the combination together for more than one hour in a blender.

In one embodiment, the method further includes a step of blending the master blend for about 48 hours.

In another embodiment, the step of adding includes the steps of: adding to a vessel about 36% methyl salicylate as a weight percent of an amount of an odorant compound, and mixing for about five minutes; adding to the vessel about 36% corn mint oil as a weight percent of the amount of the odorant compound, and mixing for an additional about five minutes; adding to the vessel about 23% white camphor oil as a weight percent of the amount of the odorant compound and mixing for an additional about five minutes; adding to the vessel about 6% cyclodextrin compound as a weight percent of the amount of the odorant compound and mixing for an additional five minutes; and adding to the vessel about 5% eucalyptus oil as a weight percent of the amount of the odorant compound, and mixing until an intermediate mixture is uniform in composition.

According to another aspect, a method for forming a synthetic resin composition, including the steps of: selecting a first thermoplastic polymer; forming a master blend including a combination of ethylene/vinyl acetate copolymer, at least one odorant compound selected from the group consisting of a salicylic acid ester, menthol, corn mint oil, eucalyptus oil, camphor oil, and combinations thereof, and at least one scent extender compound; blending the master blend for at least one hour in a blender; and combining about 1.5 weight percent of the master blend with about 98.5 weight percent of the first thermoplastic polymer to form the synthetic resin composition.

In one embodiment, the first thermoplastic polymer includes polyethylene.

In another embodiment, the combination thereof includes about 36% methyl salicylate, about 36% corn mint oil, about 23% white camphor oil, and about 5% eucalyptus oil, all as weight percentages based on a total weight of the combinations.

In yet another embodiment, the ethylene/vinyl acetate copolymer and the at least one odorant compound and the at least one scent extender compound are present in the master blend in a co-polymer:combination weight ratio of 2:1.

According to yet another aspect, an article that repels animals including a synthetic resin composition includes: a first thermoplastic polymer; and a master blend including an ethylene/vinyl acetate co-polymer, at least one odorant compound, and at least one scent extender compound, wherein a percentage by weight of the master blend is between 1.0% and 2.0% and the percentage by weight of the first thermoplastic polymer is between 98.0% and 99.0% in the synthetic resin composition, and wherein the ethylene/vinyl acetate co-polymer is combined with the odorant compound and the scent extender compound through a blending device before being combined with the first thermoplastic polymer The foregoing and other aspects, features, and advantages of the application will become more apparent from the following description and from the claims.

DETAILED DESCRIPTION

In U.S. Pat. No. 7,811,597, GARBAGE BAG OR CONTAINER, we described a synthetic resin composition which sheds an odor that keeps away domesticated animals, especially cats and dogs, and also varmints of both fur and feather, for example rats, crows, etc. The article may be made from a synthetic resin composition including a synthetic resin and from 10 to 15,000 ppm by weight of a salicylic acid ester, menthol and/or camphor. The article may also be made from a synthetic resin composition including a synthetic resin and an odorant composition containing eucalyptus oil and one or more of a salicylic acid ester, menthol and camphor. In U.S. Pat. No. 8,734,819, ANIMAL-REPELLING SYNTHETIC RESIN COMPOSITION, we described an article, such as a container or bag for garbage, or electrical wiring insulation, which repels animals such as cats, dogs, rodents, and crows. The article is made from a synthetic resin composition including a thermoplastic polymer, and from 10 to 15,000 ppm by weight of an odorant compound such as a salicylic acid ester, menthol, corn mint oil, eucalyptus oil, and camphor, and combinations thereof. Both of the '597 and '819 patents are incorporated herein by reference in their entirety for all purposes.

In many manufacturing applications, making a product from material which includes a synthetic resin composition as was described and claimed by the '597 patent and the '819 patent is an efficient and cost effective way to repel animals which might otherwise damage the product in the field. However, while materials including a synthetic resin composition shed animal repelling odors as described, it would be desirable to further extend the odor generating properties for yet longer periods of time, referred to hereinbelow as "scent extending".

What is needed in the art is a synthetic resin composition having improved penetration of odorant into the resin that therefore can be manufactured with an overall lower level of odorant and impregnated resin, at a lower cost. What is further needed in the art is an improved method for impregnating odorant into a resin that requires less odorant, leads to more uniform distribution of odorant in the resin, and requires a lower level of master blend in the final synthetic resin composition to achieve the same or better final activity of the odorant in the article. What is still further needed in the art is a synthetic resin composition comprising a mixture of odorant compounds wherein the odorant mixture includes a scent extender such as a cyclodextrin composition to reduce the rate of odorant loss during use of the composition, thereby extending the working life of the synthetic resin composition.

Cyclodextrins have been used in commercial products to control or suppress odors, such as in deodorants to suppress the detection of odors by the human nose. That is, cyclodextrins have been previously used to encapsulate odor generating compounds for preventing odors. While seemingly detrimental to the opposite application of intentionally emitting odors to repel animals, surprisingly, we realized that in some formulations as described hereinbelow, cyclodextrins can also be used to slow, but not stop, the release of animal repelling odors. By including cyclodextrins in our synthetic resin composition formulations, we were able to adapt the successful animal repellant odor molecules from our previous work in synthetic resin compositions, into synthetic resin compositions with scent extended animal repelling odors. The cyclodextrins, now instead of preventing the desired odors, slow the release of the animal repellant odor molecules that create the odor so that the repellant effect is scent extended by a cyclodextrin scent extender, and the animal repellant odor lasts longer. Or, a same desired odor can be achieved with less volume of the synthetic resin composition.

Cyclodextrins (sometimes called cycloamyloses) are a known family of compounds made up of sugar molecules bound together in a ring (cyclic oligosaccharides). Cyclodextrins are composed of 5 or more α-D-glucopyranoside monomer units linked 1→4, as in amylose (a fragment of starch). Typical cyclodextrins contain a number of glucose monomers ranging from six to eight monomer units in a ring, creating a cone shape, e.g., α (alpha)-cyclodextrin, a 6-membered sugar ring molecule; β (beta)-cyclodextrin, a 7-membered sugar ring molecule; and γ (gamma)-cyclodextrin, an 8-membered sugar ring molecule.

An extended working life odorant-containing synthetic resin composition is described. An improved process for manufacturing an article formed from an animal-repelling synthetic resin composition, includes a composition which is formed by combining a mixture of a first thermoplastic polymer or polymer mixture and a master blend including a second thermoplastic polymer. The polymer mixture may include an elastomer such as metallocene and further may include a filler in known fashion. In one exemplary embodiment, the master blend forms between about 1% and about 2% and in some embodiments, about 1.5%, and the first thermoplastic polymer or polymer mixture forms between about 98% and about 99% and in some embodiments, about 98.5%, of the synthetic resin composition, as opposed to 2.5% master blend and 97.5% first thermoplastic polymer as taught by the prior art.

The second thermoplastic polymer may be identical with, or may differ from, the first thermoplastic polymer. In one embodiment, the first thermoplastic polymer is polyethylene and the second thermoplastic polymer is ethylene/vinyl acetate copolymer (EVA). Therefore, the ratio of the present Application is less costly to manufacture because generally the second thermoplastic polymer is considerably more expensive than the first thermoplastic polymer.

Other specific examples of a thermoplastic polymer to be used in the Application include linear low density polyethylene (LLDPE), high pressure low density polyethylene (HPLDPE), and high density polyethylene (HDPE).

Other specific examples of an elastomer to be used in the Application include ethylene/propylene rubber (EPR), very low density polyethylene (VLDPE), hydrogenated styrene/butadiene block copolymer (SEES), polybutadiene, ethylene/ester of acrylic acid copolymer, ethylene/butene copolymer, ethylene/1-hexene copolymer, ethylene/1-octene copolymer, butadiene/styrene copolymer, isoprene/styrene copolymer, and hydrogenated isoprene/styrene copolymer.

Specific examples of a filler to be used in the Application include diatomaceous earth, silica gel, synthetic zeolite, aluminum oxide, hydrotalcite, calcium carbonate, talc, natural zeolite, wollastonite, calcium sulfate, magnesium hydroxide, aluminum hydroxide, titanium dioxide, and carbon black.

Specific examples of a scent extender to be used in the Application are alpha-, beta-, and gamma-cyclodextrins and chemical derivatives thereof, used singly or in combinations.

Articles such as garbage bags, wraps, containers, and cable insulation may be formed from the synthetic resin composition of the Application by any of the procedures known in the art.

The mixed pellets may be formed into blown film, as is known in the art. For example, the mixed pellets may be formed into blown film by inflation processing at 180° C. The blown film may thereafter be cut and formed into bags by bottom sealing, as is known in the art.

Alternatively, the mixed pellets may be extruded and pelletized. The thus obtained homogenized composition may be formed into strips of film by compression molding.

In certain embodiments, the synthetic resin composition may include one or both of eucalyptus oil and mint oil or corn mint oil as part of an odorant composition and further may include at least a salicylic acid ester, e.g., methyl salicylate, and camphor oil. In some embodiments, the master blend may include an intermediate odorant mixture containing from about 32% to about 40% by weight of methyl salicylate, in some embodiments, about 36%; from about 32% to about 40% by weight of corn mint oil, in some embodiments, about 36%; from about 19% to about 27% by weight of camphor oil, in some embodiments, about 23%; from about 1% to about 8% by weight of eucalyptus oil, in some embodiments, about 5%; and from about 1 part in 12 to about 1 part in 24 of a scent extender with respect to the combination of odorant compounds, all based on the total weight of the odorant mixture.

In one exemplary embodiment, a method for forming a master blend of the present Application comprises the following steps: a) selecting an amount of a thermoplastic polymer defined hereinabove as the second thermoplastic polymer, in some embodiments, ethylene/vinyl acetate copolymer; b) combining an amount of a scent extender with a plurality of compounds selected from the group consisting of a salicylic acid ester (in some embodiments, methyl salicylate), corn mint oil, eucalyptus oil, and camphor oil to form an intermediate odorant mixture; c) adding an amount of the intermediate odorant mixture to the thermoplastic polymer amount in a weight ratio of about 1:2 to form said master blend.

In some embodiments, at ambient temperature the methyl salicylate is added to a mixing kettle and mixed for 5 minutes; the corn mint oil is added and the combination is mixed for another 5 minutes; the camphor white oil is added and the combination is mixed for another 5 minutes; the scent extender is added and the combination is mixed for another five minutes; and the eucalyptus oil is added and the combination is mixed for another 5 minutes.

In a further processing step, the assembled master blend of odorant mixture and thermoplastic polymer is blended for up to 48 hours in a high-efficiency blender such as a ribbon blender, which is believed to ensure substantially uniform distribution of the odorant mixture throughout the thermoplastic polymer of the master blend.

It has been found that when the master blend is prepared in this fashion, a weight ratio of about 2 parts thermoplastic polymer to about 1 part odorant mixture, as opposed to the ratio of 4:1 taught in the prior art, provides the same or better animal-repelling effect at lower materials cost of thermoplastic polymer; and further, that the incorporation of a scent extender such as a cyclodextrin compound extends the animal-repelling working lifetime of the resin composition. An exemplary scent extender comprises at least one of alpha-cyclodextrin, beta-cyclodextrin, hydroxypropyl-beta-cyclodextrin; and methyl-beta-cyclodextrin.

From the foregoing description, it will be apparent that there has been provided an improved animal-repelling garbage bag or other article, and an improved method for forming a synthetic resin composition usable in forming such a garbage bag or other article. Variations and modifications of the herein described product and method for forming, of the invention, will undoubtedly suggest themselves to those skilled in this art. Accordingly, the foregoing description should be taken as illustrative and not in a limiting sense.

Briefly described, the Application is directed to an article, such as a container or bag for garbage, stretch wraps, shrink wraps, or wiring insulation, which repels attack by animals such as cats, dogs, rats, squirrels, raccoons, and crows. The article is made from a synthetic resin composition including a thermoplastic polymer, and from 10 to 15,000 ppm by weight of a compound such as a salicylic acid ester, menthol, corn mint oil, eucalyptus oil, and camphor, and combinations thereof. The resin composition may comprise more than one thermoplastic polymer, wherein polyethylene and ethylene/vinyl acetate are examples suitable to be used as the first and second thermoplastic polymers.

As used herein, the terms "polymer" and "resin" may be used interchangeably.

EXAMPLE

An article that repels animals comprises a synthetic resin composition that includes a first thermoplastic polymer and a master blend including a second thermoplastic polymer; at least one odorant compound selected from the group consisting of a salicylic acid ester, menthol, corn mint oil, eucalyptus oil, camphor oil, and combinations thereof; and a scent extender, wherein the ratio by weight of the second thermoplastic polymer to the combined one or more odorant compounds and scent extender in the master blend is about 2:1, and wherein after forming the article the combined one or more odorant compounds and scent extender is substantially uniformly distributed in the synthetic resin composition at between about 10 parts per million and about 15,000 parts per million by weight based on the total weight of the synthetic resin composition. In some embodiments, a scent extender of the present Application comprises at least one cyclodextrin compound.

In a general method for forming the synthetic resin composition, the one or more combined odorant compounds and scent extender are added to the second polymer in a ratio of about 1:2 parts by weight to form a master blend. The master blend then is added to the first polymer at a master blend percentage of about 1.5%. In some embodiments, the ratio of the scent extender to one or more odorant compounds is between about 1:12 and about 1:24, and in some embodiments, about 1:17.

An exemplary method for forming the synthetic resin composition comprises the steps of selecting first and second thermoplastic polymers; forming a master blend including the second thermoplastic polymer and a plurality of compounds selected from the group consisting of a salicylic acid ester, menthol, corn mint oil, eucalyptus oil, camphor oil, and a scent extender, in some embodiments, a cyclodextrin compound; blending the master blend for about 48 hours in a ribbon blender; and blending an amount of the master blend with the amount of the first thermoplastic polymer to form the synthetic resin composition It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. An article that repels animals, comprising a synthetic resin composition including:
   a first thermoplastic polymer; and
   a master blend combined with said first thermoplastic polymer, said master blend including a second thermoplastic polymer, at least one odorant compound selected from the group consisting of a salicylic acid ester, menthol, corn mint oil, eucalyptus oil, camphor oil, and combinations thereof, and at least one scent extender compound comprising at least one cyclodextrin compound,
   wherein a ratio by weight of said second thermoplastic polymer to a combination of said odorant compound and said scent extender compound is about 2:1.

2. The article of claim 1, wherein said scent extender compound comprises at least one of: alpha-cyclodextrin, beta-cyclodextrin, hydroxypropyl-beta-cyclodextrin, and methyl-beta-cyclodextrin.

3. The article of claim 1, comprising a synthetic resin composition at between about 10 parts per million and about 15,000 parts per million by weight based on a total weight of said synthetic resin composition.

4. The article of claim 1, wherein said combination thereof comprises, by weight, 32% to 40% methyl salicylate, 32% to 40% by weight of corn mint oil, 19% to 27% by weight of camphor oil, and 1% to 8% by weight of eucalyptus oil, all based on a total weight of said combination thereof.

5. The article of claim 4, wherein said combination thereof comprises, by weight, about 36% methyl salicylate, about 36% corn mint oil, about 23% white camphor oil, and about 5% eucalyptus oil all based on a total weight of said combinations thereof.

6. The article of claim 1, wherein said article is selected from the group consisting of garbage bag, stretch wrap, shrink wrap, and electrical wiring insulation.

7. The article of claim 1, wherein said first thermoplastic polymer includes a polyolefin or a polyethylene.

8. The article of claim 1, wherein said first thermoplastic polymer includes an elastomer.

9. The article of claim 8, wherein said elastomer is selected from the group consisting of ethylene/propylene rubber (EPR), very low density polyethylene (VLDPE), hydrogenated styrene/butadiene block copolymer (SEES), polybutadiene, ethylene/ester of acrylic acid copolymer, ethylene/butene copolymer, ethylene/1-hexene copolymer, ethylene/1-octene copolymer, butadiene/styrene copolymer, isoprene/styrene copolymer, and hydrogenated isoprene/styrene copolymer.

10. The article of claim 1, wherein said second thermoplastic polymer includes a polyolefin or an ethyl/vinyl acetate copolymer.

11. The article of claim 1, wherein said synthetic resin composition further comprises a filler.

12. An article of claim 11, wherein said filler is selected from the group consisting of diatomaceous earth, silica gel, synthetic zeolite, aluminum oxide, hydrotalcite, calcium carbonate, talc, natural zeolite, wollastonite, calcium sulfate, magnesium hydroxide, aluminum hydroxide, titanium dioxide, and carbon black.

13. A method for forming a master blend, comprising:
   selecting an amount of a pelleted ethylene/vinyl acetate copolymer; and
   adding a combination of an amount of a scent extender and an amount of at least one odorant compound selected from the group consisting of a salicylic acid ester, menthol, corn mint oil, eucalyptus oil, camphor oil, and combinations thereof to said pelleted ethylene/vinyl acetate copolymer in a weight ratio of 2 parts combination to 1 part ethylene/vinyl acetate copolymer, and
   blending said pelleted ethylene/vinyl acetate copolymer and said combination together for more than one hour in a blender.

14. The method of claim 13, further comprising a step of blending said master blend for about 48 hours.

15. The method of claim 13, wherein said step of adding includes the steps of:
   adding to a vessel about 36% methyl salicylate as a weight percent of an amount of an odorant compound, and mixing for about five minutes;

adding to said vessel about 36% corn mint oil as a weight percent of said amount of said odorant compound, and mixing for an additional about five minutes;

adding to said vessel about 23% white camphor oil as a weight percent of said amount of said odorant compound and mixing for an additional about five minutes;

adding to said vessel about 6% cyclodextrin compound as a weight percent of said amount of said odorant compound and mixing for an additional five minutes; and adding to said vessel about 5% eucalyptus oil as a weight percent of said amount of said odorant compound, and mixing until an intermediate mixture is uniform in composition.

16. A method for forming a synthetic resin composition, comprising:

selecting a first thermoplastic polymer;

forming a master blend including a combination of ethylene/vinyl acetate copolymer, at least one odorant compound selected from the group consisting of a salicylic acid ester, menthol, corn mint oil, eucalyptus oil, camphor oil, and combinations thereof, and at least one scent extender compound;

blending said master blend for at least one hour in a blender; and combining about 1.5 weight percent of said master blend with about 98.5 weight percent of said first thermoplastic polymer to form said synthetic resin composition.

17. The method of claim 16, wherein said first thermoplastic polymer comprises polyethylene.

18. The method of claim 16, wherein said combination thereof comprises about 36% methyl salicylate, about 36% corn mint oil, about 23% white camphor oil, and about 5% eucalyptus oil, all as weight percentages based on a total weight of said combinations.

19. The method of claim 16, wherein said ethylene/vinyl acetate copolymer and said at least one odorant compound and said at least one scent extender compound are present in said master blend in a co-polymer:combination weight ratio of 2:1.

20. An article that repels animals including a synthetic resin composition comprises:

a first thermoplastic polymer; and a master blend including an ethylene/vinyl acetate co-polymer, at least one odorant compound, and at least one scent extender compound, wherein a percentage by weight of said master blend is between about 1.0% and 2.0% and the percentage by weight of said first thermoplastic polymer is between about 98.0% and 99.0% in said synthetic resin composition, and wherein said ethylene/vinyl acetate co-polymer is combined with said odorant compound and said scent extender compound through a blending device before being combined with said first thermoplastic polymer.

* * * * *